United States Patent
Toyoshima et al.

(10) Patent No.: US 7,288,079 B2
(45) Date of Patent: Oct. 30, 2007

(54) DISPOSABLE DIAPER CAPABLE OF BEING PUT ON EITHER FROM THE FRONT OR THE BACK OF A WEARER

(75) Inventors: Haruko Toyoshima, Tochigi (JP); Yasuyuki Okuda, Tochigi (JP)

(73) Assignee: Kao Corporation, Tokyo (JP)

( * ) Notice: Subject to any disclaimer, the term of this patent is extended or adjusted under 35 U.S.C. 154(b) by 997 days.

(21) Appl. No.: 10/626,673

(22) Filed: Jul. 25, 2003

(65) Prior Publication Data
US 2007/0191808 A1    Aug. 16, 2007

(30) Foreign Application Priority Data
Jul. 26, 2002  (JP)  ............... 2002-218964
Feb. 4, 2003   (JP)  ............... 2003-027634

(51) Int. Cl.
*A61F 13/15*  (2006.01)
*A61F 13/20*  (2006.01)

(52) U.S. Cl. ............... 604/385.01; 604/385.03; 604/385.29; 604/385.3; 604/385.21; 604/389; 604/391; 604/392

(58) Field of Classification Search ........... 604/385.03, 604/385.29, 385.3, 385.21, 389, 391, 392
See application file for complete search history.

(56) References Cited

U.S. PATENT DOCUMENTS

| | | | |
|---|---|---|---|
| 4,050,462 A | 9/1977 | Woon et al. | |
| 5,944,707 A | 8/1999 | Ronn | |
| 2002/0151863 A1* | 10/2002 | Toyoshima | 604/385.29 |
| 2004/0215161 A1* | 10/2004 | Okuda et al. | 604/385.28 |
| 2004/0243090 A1* | 12/2004 | Toyoshima et al. | 604/389 |
| 2007/0038198 A1* | 2/2007 | Wada | 604/385.3 |

FOREIGN PATENT DOCUMENTS

| | | |
|---|---|---|
| EP | 1184012 A1 | 3/2002 |
| EP | 1188427 A1 | 3/2002 |
| EP | 1226802 A2 | 7/2002 |
| JP | 52-120045 | 10/1977 |
| JP | 1-141711 | 9/1989 |
| JP | 2-164363 A | 6/1990 |
| JP | 6-63077 A | 3/1994 |
| JP | 2000-254167 A | 9/2000 |
| WO | WO95/12376 A1 | 5/1995 |
| WO | WO00/53140 A1 | 9/2000 |
| WO | WO01/34084 A1 | 5/2001 |

* cited by examiner

*Primary Examiner*—Tatyana Zalukaeva
*Assistant Examiner*—Ginger Chapman
(74) *Attorney, Agent, or Firm*—Birch, Stewart, Kolasch & Birch, LLP (57) ABSTRACT

A disposable diaper capable of being put on from either the front or the back of a wearer. The ratio of the minimum width W1 of the crotch section to the whole width W2 of the longitudinal end section having the fastening tapes is from 0.30 to 0.75. The minimum width W1 is in the area extending from the centerline across the diaper that divides the diaper length in two equal halves toward both the longitudinal end sections thereof by ±10% of the total length of the diaper. The area ratio S1/S2 is from 0.45 to 0.60, where S1 is the area of each region surrounded by an imaginary straight line L1, an imaginary straight line L2, and each arched side edge of the crotch section, and S2 is the area of each region surrounded by the line L1, the line L2, and an imaginary straight line L3.

6 Claims, 5 Drawing Sheets

wearer's stomach side    wearer's back side

Fig.4(b)

wearer's stomach side    wearer's back side

DISPOSABLE DIAPER CAPABLE OF BEING PUT ON EITHER FROM THE FRONT OR THE BACK OF A WEARER

BACKGROUND OF THE INVENTION

The present invention relates to a disposable diaper that can be easily put on a wearer in either case where the fastening tapes are fastened on the wearer's stomach side or where they are fastened on a wearer's back side, that can be easily put on whether the wearer is standing or lying, and that hardly impedes the wearer's movement while worn.

Known disposable diapers include fitted diapers having fastening tapes and pull-on diapers (also called pants type diapers or all-in-ones) that can be put on like ordinary underwear. Fitted disposable diapers are most commonly used in view of both their applicability to a full range of children, from newborns to toddlers, and because of their lower production cost.

A fitted disposable diaper is easy to put on a wearer such as a baby or an infant who is lying still on its back. However, it is not easy to put on an infant who is active enough to, for example, crawl about, being reluctant to wear a diaper, or have a new diaper put on.

Pull-on diapers are on the market for infants who can walk, but those suited for babies who have mastered crawling and are now on to pulling up themselves are not available yet. Even after a baby becomes able to pull itself up on something into a standing position, it is practically difficult to make the baby raise one foot to put on a pull-on diaper.

Hence, the present inventors have attempted to use a conventional fitted disposable diaper which is designed to be fastened on the stomach side in a back-to-front manner, that is, put on the diaper with its portion that is to be disposed on the wearer's back being applied to the stomach side. However, a conventional fitted disposable diaper is difficult to put on back to front, and, when fitted back to front, it is less capable of exhibiting its absorbing ability and more liable to leak while being worn.

JP-A-6-63077 proposes a diaper which is designed to be fastened with fastening tapes on the wearer's back side. The diaper has an elastic flap on each side of the stomach portion and a fastening tape fixed to each of the elastic flaps and enjoys ease of fastening on the wearer's back side as compared with traditional fitted disposable diapers. Nevertheless one often finds it convenient to fix fastening tapes on the wearer's front side. Therefore a diaper configured exclusively for fastening on the back side cannot avoid sacrificing ease to put on the front side, absorbing performance and leakproofness when used in an ordinary manner (i.e., fastened on the front side). The diaper of JP-A-6-63077 is designed for fastening only on the wearer's back side for application to infants who have developed to move actively and therefore gives no considerations to front side fastening usage.

JP-A-2-164363 proposes a diaper cover which is designed to be fastened with fastening tapes on the wearer's back side. WO95/12376 discloses a diaper having a pair of fastening ears which extend to the wearer's back side.

These proposed diaper cover and diaper are designed to be fastened on the back side and are therefore given no considerations to front side fastening usage.

Thus, a disposable diaper that sufficiently satisfies the ease of putting on as well as the absorption requirement when fastened on either side has not yet been proposed.

SUMMARY OF THE INVENTION

The present invention relates to a disposable diaper capable of being put on from either the front or the back of a wearer which includes:

a liquid permeable topsheet, a liquid impermeable backsheet, a liquid retentive absorbent member interposed between the topsheet and the backsheet, the diaper having a pair of longitudinal side portions and a pair of longitudinal end sections, with each respective side portion and end section having a side edge, and a crotch section having two side edges being positioned between the pair of longitudinal end sections, with each of the crotch section's two side edges containing an arched side edge, a fastening tape provided on each respective side edge of each longitudinal end section, and each longitudinal side section of the diaper containing both a standing gather and a leg gather; provided that:

a ratio of the minimum width W1 of the crotch section of the diaper to a whole width W2 of the longitudinal end section having the fastening tapes provided on each side edge thereof is from 0.30 to 0.75, the minimum width W1 is in an area extending from a centerline across the diaper that divides a total length of the diaper in two equal halves toward both the longitudinal end sections thereof by ±10% of the total length of the diaper, and an area ratio of S1 to S2 is from 0.45 to 0.60, where S1 is an area of a region surrounded by an imaginary straight line L1 which passes through a midpoint P on one of the arched side edges of the crotch section of the diaper, in which the crotch section is divided into equal halves, an imaginary straight line L2 which intersects with the line L1 at right angles and passes through an end point Q of the arched side edge of the crotch section on a side of the crotch section nearest the longitudinal end section of the diaper having the fastening tapes provided on each side edge thereof, and the arched side edge of the crotch section, and S2 is an area of a region surrounded by the line L1, the line L2, and an imaginary straight line L3 which connects the midpoint P and the end point Q.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

FIG. 4(a) and FIG. 4(b) illustrate how to put the disposable diaper of FIG. 1 on a standing infant, in which FIG. 4(a) shows stomach side fastening, and FIG. 4(b) shows back side fastening;

FIG. 6(a) and FIG. 6(b) are enlarged views of a fastening tape used in the disposable diaper shown in FIG. 5, in which FIG. 6(a) is a plan, and FIG. 6(b) is a cross-section taken along line X-X of FIG. 6(a).

DETAILED DESCRIPTION OF THE PREFERRED EMBODIMENTS

The present invention will be described in detail with reference to its preferred embodiment. All publications cited herein are hereby incorporated by reference.

The present invention relates to a disposable diaper that can be easily put on a wearer in either case where the fastening tapes are fastened on the wearer's stomach side or where they are fastened on wearer's back side, and that hardly impedes the wearer's movement while worn.

The expression "a disposable diaper capable of easily being put on either from the front or the back of a wearer" as referred to herein means that a diaper can be easily put on a wearer in either case where the fastening tapes are fastened on the wearer's stomach side (referred to as "stomach side fastening" hereinafter) or where the fastening tapes are fastened on wearer's back side (referred to as "back side fastening" hereinafter).

Figure 1:
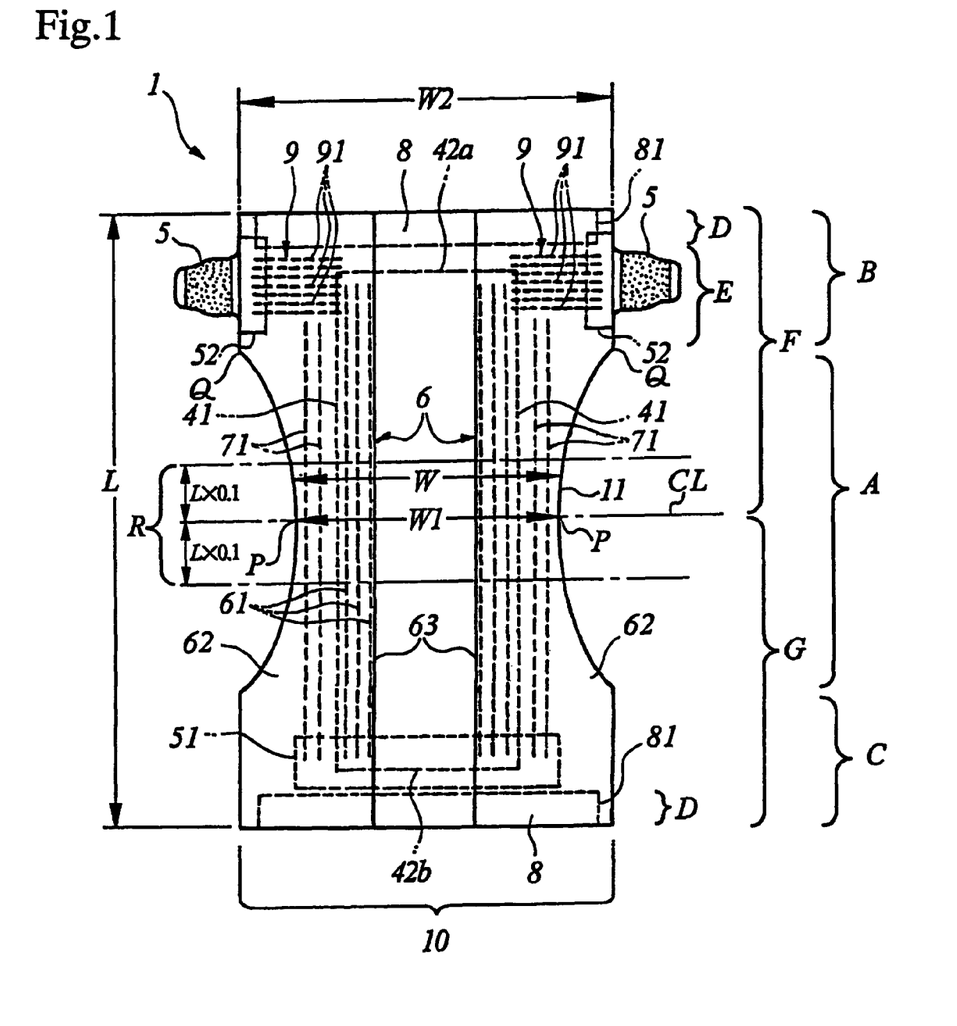
FIG. 1 is a plan of a disposable diaper according to an embodiment of the present invention with its elastic members being in their substantially stretched flat state.
Figure 2:
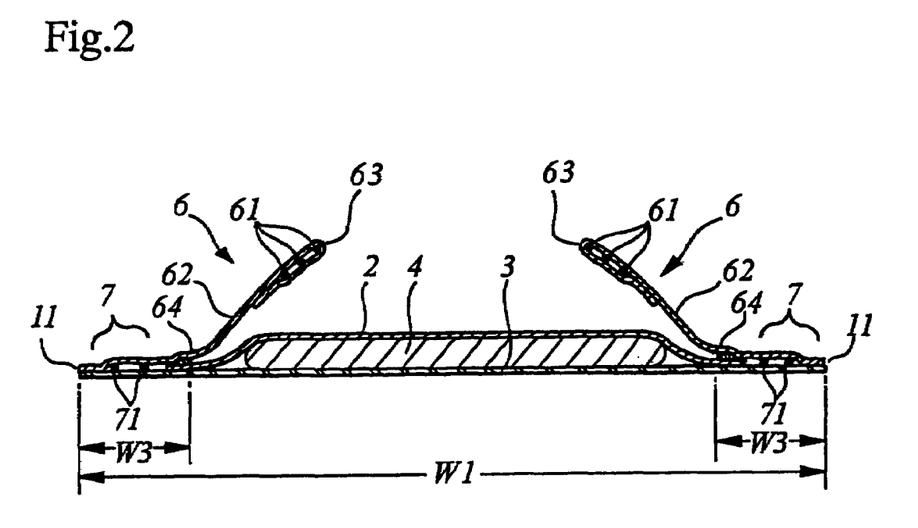
FIG. 2 is a schematic cross-section of the disposable diaper of FIG. 1, taken along a line in which the crotch section is narrowest (a centerline dividing the length of the diaper into two equal halves)

A preferred embodiment the present invention provides a disposable diaper 1 shown in FIGS. 1 and 2 which comprises a liquid permeable topsheet 2, a liquid impermeable backsheet 3, and a liquid retentive absorbent member 4 interposed between these two sheets. The disposable diaper 1 is of a fitted type for infants. It is divided, in its longitudinal direction, into a crotch section A in the middle in the length direction, a first section B on one side of the crotch section A, and a second section C on the other side of the crotch section A. The first section B has a pair of fastening tapes 5 respectively provided on each side edge, and the second section C has a landing zone 51 for receiving the fastening tapes 5. The crotch section A is applied to the crotch of a wearer.

The crotch section A describes an inward arc on both sides thereof. The disposable diaper 1 as a whole has a sand glass shape with its longitudinal middle portion narrowed.

The topsheet 2 is substantially rectangular and larger than the absorbent member 4 when viewed from above. The absorbent member is arranged in the middle in the width direction of the backsheet 3. The backsheet 3 is sand glass-shaped in agreement with the contour of the diaper 1.

The topsheet 2 and the backsheet 3 both extend outward from the two longer sides 41 and two shorter sides 42a and 42b of the absorbent member 4 and are bonded together in these extensions. The backsheet 3 extends outward from the two longer sides of the topsheet 2.

Elastic members are disposed on both longer side areas of the diaper 1 to create a pair of standing gathers (or cuffs) 6 and a pair of leg gathers 7. Going into detail, the pair of standing gathers are each formed of a gather-forming sheet 62 having elastic members 61, the gather-forming sheet 62 being disposed to cover both side areas of the longer side edge of the topsheet 2. Each sheet 62 is fixed to the topsheet 2 in a straight line pattern parallel to the diaper longitudinal direction between the side edge 41 of the absorbent member 4 and the laterally most inward elastic member 71 arranged in the leg portion (described later). The sheet 62 is fixed to the topsheet 2 by known bonding means, such as a heat seal or an adhesive. The linear joint of the sheet 62 with the topsheet 2 is a fixed end 64 of the standing gathers 6. The part of the sheet 62 extending outward from the fixed end 64 is fixed to the topsheet 2 or the backsheet 3. In the areas near the two longitudinal ends of the diaper 1, the part of the sheet 62 extending inward from the fixed end 64 is fixed to the topsheet. The elastic members 61 used to form the standing gathers 6 are strings. A plurality of the elastic members (strings) 61 are arranged per side substantially in parallel with the free end 63 of the standing gathers.

The pair of leg gathers 7 are each formed by almost linearly arranging a plurality of elastic members 71 on the area extending outward from the fixed end 64 of the standing gathers 6.

All of the elastic members 61 and 71 are disposed along the longitudinal direction of the diaper 1 over a length including part of the first section B, the section A, and part of the section C.

The first section B includes a waist portion D, where an elastic member 81 is provided to form an extensible waist part 8. In this embodiment, the second section C also has an elastic member 81 to form an extensible waist part 8 in its waist portion D. Each waist portion D constitutes the longitudinal end of the diaper 1 and is applied to the waist of a wearer.

The disposable diaper 1 also has a pair of extensible side parts 9 discretely provided in the area between the two fastening tapes 5 attached to the side flaps of the first section B. The extensible side parts 9 are each elastically extensible and contractible in the diaper width direction. The side flaps as referred to above are regions extending outward in the diaper width direction from each side edge 41 of the absorbent member 4. The area between the two fastening tapes as referred to above means the area between a pair of joint areas 52 where one end of each fastening tape is fixed to the main part 10 of the diaper 1 (see FIG. 1). The term "main part (10) of the diaper (1)" as used herein means the part composed of the topsheet 2, the backsheet 3, and the absorbent member 4 and including all the sections A to C.

The two extensible side parts 9 are discretely formed on each side in the diaper width direction in the first section B of the diaper. That is, such an extensible part that extends and contracts elastically in the diaper width direction is not formed in the middle portion in the width direction between the fastening tapes 5.

Going into details, elastic members 91 are fixed in their stretched state such that elastic extensibility may develop in at least areas extending outward from both side edges 41 of the absorbent member 4 in the diaper width direction. Elastic members 91 are not arranged in the middle portion of the area between the side edges 41 of the absorbent member 4. The elastic members 91 are fixedly sandwiched in between two soft sheets (not shown) which are provided in the first section B over the width of the main body 10. The two sheets are fixed by bonding between the backsheet 3 or the absorbent member 4 and the topsheet 2 or the gather-forming sheet 62. The inward end of each elastic member 91 is positioned slightly inward from the side edge 41 of the absorbent member 4. Therefore, there is no elastic member in the area from the middle in the width direction of the absorbent member 4 up to a point near each side edge 41. A plurality of elastic members 91 are arranged per extensible side part 9 in parallel to the diaper width direction at prescribed intervals.

The ratio of the minimum width W1 of the crotch section A (see FIGS. 1 and 2) to the whole width W2 of the first section B (see FIG. 1), W1/W2, is from 0.30 to 0.75, preferably from 0.30 to 0.72, still preferably from 0.30 to 0.70.

The minimum width W1 of the crotch section A is defined to be the minimum of the widths W between both arched side edges 11 of the crotch section A measured along the diaper width direction (the width(s) W will hereinafter be referred to as a crotch width(s)) while the diaper 1 is in its substantially stretched flat state. If the above-identified width ratio W1/W2 is smaller than 0.30, the difference between the whole width and a crotch width is so large as to destroy the width balance that the diaper hardly fits the crotch. Where that width ratio exceeds 0.75, the diaper hardly fits the inner thighs when fastened on the wearer's back side. Where that width ratio is 0.70 or lower, the diaper easily fits the inner thighs when putting the diaper on a wearer lying on its back or stomach and is easily pulled up when putting on a wearer in a standing position.

In the present invention, the minimum width W1 must be in the area R (see FIG. 1) which extends from the centerline CL that cuts across the diaper and divides the length of the diaper in two equal halves, towards both longitudinal diaper ends by ±10% of the total length L of the diaper (see FIG. 1). The crotch width gradually increases from the area R to the end point Q of the crotch section A. In this particular embodiment shown in FIG. 1, the crotch section A becomes narrowest to have the minimum width W1 at the centerline CL.

The minimum width W1 of the crotch section A is preferably from 100 to 240 mm for assuring ease of applying the crotch portion between the thighs of a crawling or standing infant. In order to secure ease of fastening the diaper on a standing wearer by back side fastening while achieving high leakproof performance, the minimum width W1 is still preferably from 120 to 230 mm, particularly preferably from 120 to 200 mm.

Figure 3:
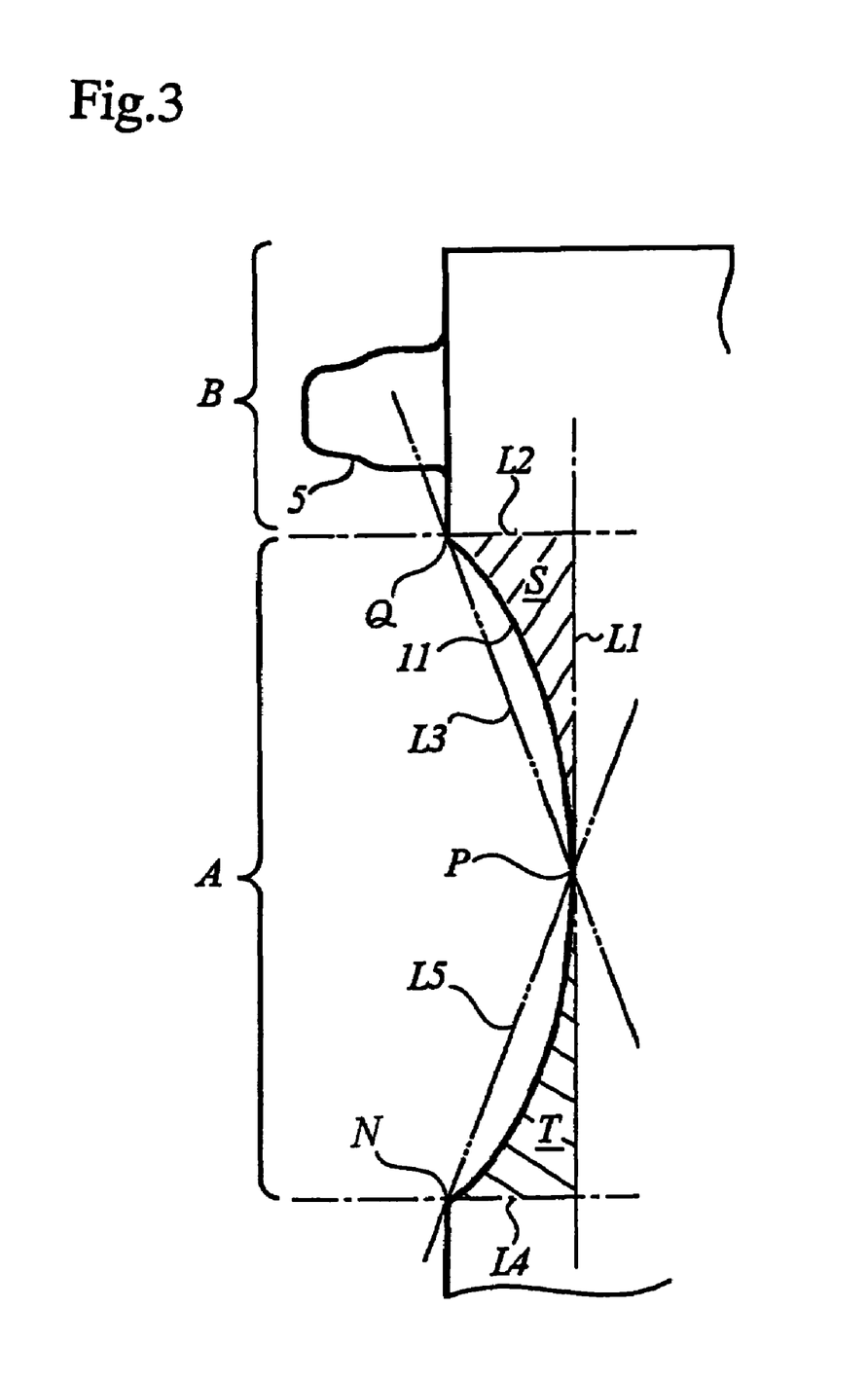
FIG. 3 is a schematic partial plan for illustrating the shape of the side flaps of the disposable diaper shown in FIG. 1.

The shape of the disposable diaper 1 according to embodiments of the present invention will be further described by referring to FIG. 3. Obtain a midpoint P on each arched side edge 11 of the crotch section A at which the length of the crotch section A is divided into equal halves. Draw an imaginary straight line L1 which passes through the midpoint P in the longitudinal direction of the diaper. Draw an imaginary straight line L2 which intersects with the line L1 at right angles and passes through the end point Q of the arched side edge 11 on the first section B side. Draw an imaginary straight line L3 which connects the midpoint P and the end point Q. The region surrounded by the lines L1 and L2 and the arched side edge 11 is designated region S.

The ratio of the area S1 of the region S to the area S2 of the right-angled triangle surrounded by the lines L1, L2 and L3, e.g. S1/S2, is from 0.45 to 0.60, preferably from 0.45 to 0.55, still preferably from 0.45 to 0.52.

In the embodiment shown in FIGS. 1 and 2, the longitudinal midpoint P on the arched side edge 11 is on the centerline CL (see FIG. 1), on which the crotch width W becomes the smallest. By this configuration, the diaper 1 enjoys the advantages that it is easily put on a wearer in either case where the fastening tapes are fastened on the wearer's stomach side or where they are fastened on wearer's back side, and fastened from either the front or the back of a wearer and that leakage hardly occurs.

If the area ratio S1/S2 is smaller than 0.45, the wearer's buttocks will be exposed when the diaper is fastened by the stomach side fastening. If it is larger than 0.60, the diaper is difficult to apply to a wearer's body when it is fastened by the back side fastening, and the diaper fastened on the wearer's back side tends to impede the wearer's movement.

The above-described relationship between the crotch section A and the flaps of the first section B also applies to the relationship between the crotch section A and the flaps of the second section C where a landing zone is provided. That is, an imaginary straight line L4 is drawn which intersects with the line L1 at right angles and passes through the end point N of the arched side edge 11 on the second section C side. The ratio of the area S3 of the region T surrounded by lines L1 and L4 and the arched side edge 11 to the area S4 of the right-angled triangle surrounded by the line L1, the line L4, and a line L5 connecting the midpoint P and the end point N, e.g. S3/S4, is preferably from 0.45 to 0.60, more preferably from 0.45 to 0.55, still even more preferably from 0.45 to 0.52. It is preferred for obtaining enhanced effects of the invention that the ratio of S1/S2 to S3/S4 be from 0.9 to 1.1, more preferably 1.

In the diaper 1 according to an embodiment of the present invention, the ratio of the distance W3 (see FIG. 2) from the fixed end 64 of the standing gathers 6 to the arched side edge 11 of the crotch section A in the minimum width W1 (i.e., the distance measured on the line having the minimum width W1 which agrees with the centerline CL) to the whole width W2 of the diaper, e.g. W3/W2, is preferably from 0.1 to 0.2. By this configuration, one can rapidly apply the diaper to the crotch of a baby or an infant trying to escape the diaper on all fours or in a standing position. In so doing, the leg flaps extending from the side edges of the absorbent member in the crotch section A are prevented from bunching up and thereby prevents leakage even when the diaper is fastened on the wearer's back side. The distance W3 is measured in parallel with the diaper width direction. It is particularly preferred that the ratio W3/W2 be from 0.10 to 0.15. This preferred W3/W4 value combined with the above-mentioned side flap constitution prevents the buttocks from being exposed and enhances the effect against leakage.

Thus, the diaper 1 of an embodiment of the present invention is characterized in that (1) W1/W2 falls within a specific range, (2) the crotch section becomes narrowest in the middle portion in the diaper longitudinal direction, and (3) the side flaps having the fastening tapes have a specific shape such that S1/S2 may fall within a specific range. These configurational features bring about improved ease to put on and fasten by the back side fastening without impairing the absorption performance and leak-proof properties essential to a diaper.

Figure 4A:
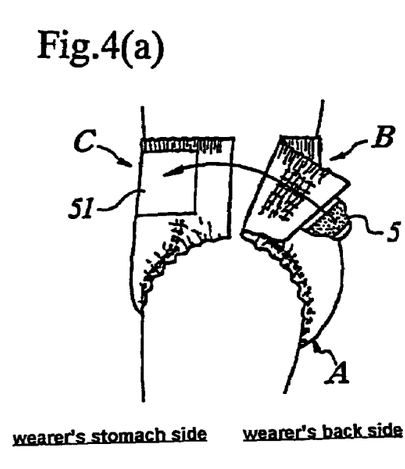
Figure 4B:
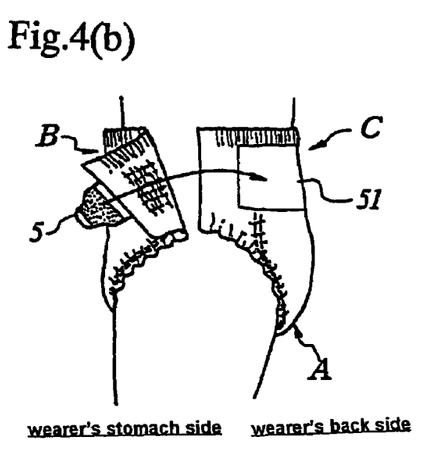

Mere reduction in the width of the crotch section of a conventional disposable diaper will result in impairment of the absorption and leak-proof performance essential to a diaper. In contrast, the embodiments of the present invention succeeds in providing a disposable diaper that is easy to put on from either side of a wearer while retaining absorption and leakproof performance by specifying the crotch section width in relation to the side flaps and specifying the shape of the side flaps. Furthermore, this specific configuration makes it possible to smoothly apply the diaper to a wearer in a standing position with a narrow space between the inner thighs. Accordingly, the diaper can easily be put on a wearer in a standing or crawling position. In particular, when a baby or infant in such a position is diapered from behind (see FIG. 4(a)), the diaper with its side flaps having fastening tapes 5 being so designed as described above will not hinder the movement of the diapered wearer's legs. Moreover, in diapering a wearer in a standing position from the stomach side (see FIG. 4(b)), the wearer's buttocks will not be exposed more than as necessary.

Since the side flaps of the diaper 1 according to an embodiment of the present invention each have the extensible side part 9, sufficient extensibility around the body can be secured even if the side flaps are made narrower than those in conventional disposable diapers. As a result, the diaper hardly slides down, there is minimum exposure of the buttocks, and it hardly causes leaks.

Dividing crosswise the disposable diaper 1 of the present embodiment into two equal halves F and G at the centerline CL (see FIG. 1), the ratio of saturated absorption capacity of the halves, F/G, ranges preferably from 45/55 to 55/45. Therefore, urine leakage does not occur even where the diaper is put on and fastened from the back of a wearer.

That is, the disposable diaper 1 according to an embodiment of the present invention can be put on with ease either from the front or the back of a wearer and does not leak in either case. In order to further improve leak prevention irrespective of the diapering direction, the F/G saturated absorption capacity ratio is preferably from 48/52 to 52/48. The smaller the difference in saturated absorption capacity between the F and G sections, the more preferred for leak prevention.

The saturated absorption capacity of the section on each side of the centerline CL is measured as follows.

Method of Measuring Saturated Absorption Capacity:

A diaper 1 is cut across into two along the centerline CL, the line dividing the diaper length into equal halves. The standing gathers and the leg gathers are cut off from each section. Care should be taken to keep the structure of the absorbent member intact. The cut piece is placed on a metal net which is configured to be taken out of a container horizontally. The metal net with the cut piece on is weighed and then put in a container having a drain hole in the lower part of one side thereof. The drain hole is closed, and 0.9 wt % of a physiological saline is poured to completely immerse the absorbent member at a rate controlled so that polymer particles and the like may not fall off from the cut edge of the diaper. After being completely immersed, the cut piece is allowed to stand for 30 minutes. The container is tilted 10° with the drain hole side down, and the drain hole is opened to discharge the liquid. The container is kept tilted for 30 minutes until the liquid is completely drained. The metal net with the cut piece on is taken out of the container and weighed again. The difference between the weight after immersion and the weight before immersion is taken as a saturated absorption capacity (g) of the cut piece.

Materials of the members making up the disposable diaper 1 according to an embodiment of the present invention will now be described.

The materials for forming the topsheet 2, the backsheet 3, the absorbent member 4, the standing gather—forming sheet 62, the landing zone 51—forming landing tape, and the like are not limited and selected appropriately from known materials commonly used in conventional disposable diapers.

The fastening tape 5 includes a tape having a male member (hook) 5a of a mechanical fastener and a tape having a self-adhesive layer formed by applying a self-adhesive. Where the outer surface of the backsheet 3 is made of an engageable material, that surface can serve as a landing zone 51.

The elastic members 61, 71, 81, and 91 for forming the standing gathers 6, the leg gathers 7, the extensible waist parts 8, and the extensive side parts 9, respectively, are known and conventional. Useful forms of these elastic members include strings, bands of some width, and films. Materials of the elastic members include natural rubber, synthetic rubbers (e.g., styrene-butadiene, butadiene, isoprene or neoprene rubbers), ethylene-vinyl acetate copolymers, extensible polyolefins, and urethane rubber.

While the present invention has been described in detail and with reference to a specific preferred embodiment thereof, various changes and modifications can be made therein without departing from the spirit and the scope thereof.

Figure 5:
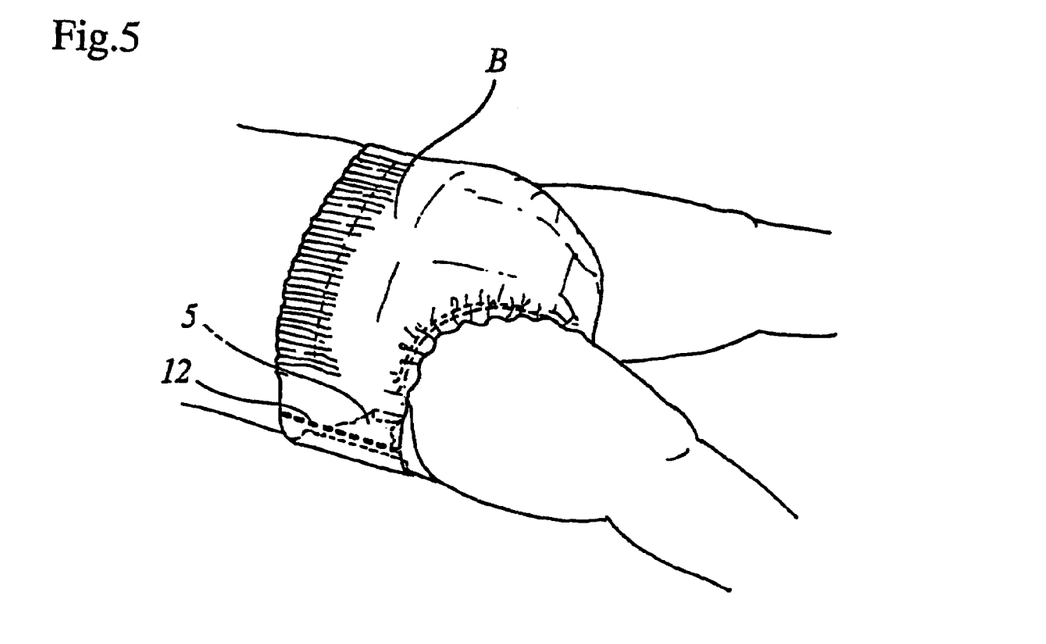
FIG. 5 is a partial perspective of an infant lying on its back and wearing a disposable diaper according to another embodiment of the present invention, the diaper having been put on the infant by back side fastening.

For example, perforations 12 for tearing may be made on both side parts of the diaper that come to the wearer's sides. The perforations 12 will provide a solution to the hard-to-remove problem accompanying a diaper fastened on the back side. In detail, where a disposable diaper is fastened by back side fastening, one may feel like making a wearer lie on its stomach to change diapers. Where a baby has passed stools, however, such way of diaper exchange will allow the stools to move toward the stomach side, only to needlessly soil the urethra orifice or the genital organ. Therefore, diapers are usually changed while a baby is lying on its back as illustrated in FIG. 5. As shown, because the fastening tapes 5 are underneath the body, it is not easy to pick up and peel the fastening tapes 5. The perforations 12 allow the diaper be torn at both sides with ease, making it possible for one to remove the dirty diaper easily without soiling the urethra orifice and the genital organ with stools. The pattern and the position of the perforations are not limited as far as the purpose is achieved.

Figures 6A, 6B:
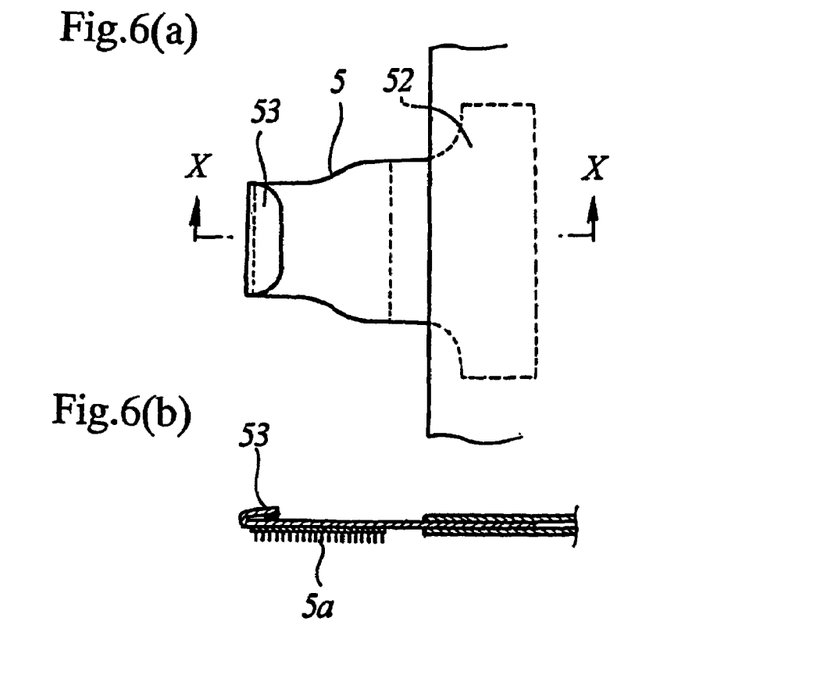

As shown in FIG. 6, the free end of each fastening tape 5 may be turned up. The turn-up 53 shown in FIG. 6 is formed by folding back the free end of the tape to the side opposite to the fastening side (indicated by numeral 5a) of the tape. The turn-up 53 is removably adhered to the facing area via a self-adhesive so that it may be stripped and picked up in peeling the fastening tape from the landing zone. The removable turn-up makes it easier for one to pick up and peel the fastening tape off the landing zone in removing a soiled diaper that has been fastened on the wearer's back side while the wearer is lying on its back. The turn-up does not always need to be removably adhered to the facing area and could be one that has simply been folded back to make a crease.

The perforations for diaper tearing and the turn-up of the fastening tapes are applicable to not only the disposable diaper according to the above-described embodiment but to disposable diapers having other structures enabling fastening from the back, preferably those diapers meeting one or more constitutional requirements of the above embodiment.

The disposable diaper according to the present invention is suited for babies, especially those who are prone to hate or dislike being diapered.

EXAMPLE 1 AND COMPARATIVE EXAMPLES
1 TO 3

The following examples further describe and demonstrate embodiments of the present invention. The examples are given solely for the purpose of illustration and are not to be construed as limitations of the present invention.

Disposable diapers shown in FIGS. 1 and 2 were prepared. The dimensions, areas, ratios, etc. of the sections or regions making up the diapers are shown in Table 1.

Evaluation of Performance:

The diapers prepared were evaluated for (1) ease to put on a wearer in a standing position by back side fastening, (2) non-hindrance to legs' movement (ease for a wearer to move its legs), and (3) protection against leaks from the crotch portion of a moving wearer (leakproofness in motion) according to the test methods described below. The results obtained are shown in Table 1.

(1) Ease to Put on from the Back

The diaper was put on a standing infant, and the fastening tapes were fastened to the landing zone on the back side of the infant. The ease to diaper in this manner of diapering was evaluated as follows.

Good: The diaper was put on with its waist end kept on the level with the navel without sliding down during fastening from the back.

Bad: The diaper was put on with its waist end below the navel because it slid down during fastening from the back.

(2) Non-Hindrance to Legs' Movement

A simulated infant hip model was used for testing. The model is shaped to the hips and buttocks of an infant in a standing position and is designed to perform a walking movement and to discharge artificial urine through a tube from the crotch. The diaper was put on the model and fastened from the back side of the model. The diapered model was operated to make a walking movement, and the walking movement of the model was observed to evaluate the non-hindrance to legs' movement.

Good: The side flaps cause no hindrance to the legs' movement.

Bad: The side flaps cause hindrance to the legs' movement.

(3) Leakproofness in Motion

A disposable diaper was put on the same infant hip model as used in (2) above with its front waist end level with the navel by the back side fastening. The model was made to make a 5-minute walking movement at a pace of 150 steps per minute. After stopping the walking movement, 80 g of artificial urine was poured through the tube at a rate of 5 g/sec, and the model was again made to make the same walking movement for 5 minutes. Then the model was laid on its side, and 40 g of artificial urine was poured at a rate of 5 g/sec. At the time point when the pouring was completed, whether any leak occurred was inspected with the naked eye. Where no leaks was observed, an additional 40 g portion of the artificial urine was poured. Additional pouring of a 40 g portion of artificial urine was repeated until a leak occurred. The total amount of the artificial urine poured until leakage was taken as a measure of leakproofness in motion.

TABLE 1

|  | Example 1 | Comparative Example | | |
|---|---|---|---|---|
|  |  | 1 | 2 | 3 |
| Minimum Crotch Width W1 (mm) | 225 | 244 | 235 | 220 |
| Whole Width W2 (mm) | 315 | 315 | 310 | 320 |
| Width Ratio W1/W2 | 0.71 | 0.78 | 0.76 | 0.69 |
| Area S1 (cm²) | 16.6 | 10.8 | 8.8 | 13.2 |
| Area Ratio S1/S2 | 0.50 | 0.41 | 0.35 | 0.38 |
| Area Ratio S3/S4 | 0.50 | 0.46 | 0.22 | 0.35 |
| Width Ratio W3/W2 | 0.12 | 0.18 | 0.23 | 0.16 |
| Ease to Fasten by Back Side Fastening | good | bad | Bad | bad |
| Non-hindrance to Legs' Movement | good | bad | Bad | bad |
| Leakproofness in Motion (g) | 160 | 120 | 120 | 120 |

The disposable diaper according to embodiments of the present invention can be easily put on a wearer in either case where the fastening tapes are fastened on the wearer's stomach side or where they are fastened on the wearer's back side, particularly when fastening tapes are fastened on the wearer's back side. The diaper hardly impedes the wearer's movement while being worn, and exhibits improved properties against leaks from the crotch portion.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

This application claims the priority of Japanese Patent Application Nos. 2002-218964 filed Jul. 26, 2002 and 2003-27634 filed Feb. 4, 2003, which are incorporated herein by reference.

What is claimed is:

1. A disposable diaper capable of being put on from either the front or the back of a wearer comprising:

a liquid permeable topsheet, a liquid impermeable backsheet, a liquid retentive absorbent member interposed between the topsheet and the backsheet, said diaper having a pair of longitudinal side portions and a pair of longitudinal end sections, with each respective side portion and end section having a side edge, and a crotch section having two side edges being positioned between said pair of longitudinal end sections, with each of the crotch section's two side edges containing an arched side edge, a fastening tape provided on each respective side edge of each longitudinal end section, and each longitudinal side section of the diaper containing both a standing gather and a leg gather; provided that:

a ratio of the minimum width W1 of the crotch section of the diaper to a whole width W2 of the longitudinal end section having the fastening tapes provided on each side edge thereof is from 0.30 to 0.75, the minimum width W1 is in an area extending from a centerline across the diaper that divides a total length of the diaper in two equal halves toward both the longitudinal end sections thereof by ±10% of the total length of the diaper, and an area ratio of S1 to S2 is from 0.45 to 0.60, where S1 is an area of a region surrounded by an imaginary straight line L1 which passes through a midpoint P on one of the arched side edges of the crotch section of the diaper, in which the crotch section is divided into equal halves, an imaginary straight line L2 which intersects with the line L1 at right angles and passes through an end point Q of the arched side edge of the crotch section on a side of the crotch section nearest the longitudinal end section of the diaper having the fastening tapes provided on each side edge thereof, and the arched side edge of the crotch section, and S2 is an area of a region surrounded by the line L1, the line L2, and an imaginary straight line L3 which connects the midpoint P and the end point Q.

2. The disposable diaper according to claim 1, wherein the longitudinal end section having the fastening tape provided on each respective side edge thereof, has a pair of extensible side parts which are elastically extensible and contractible in the diaper width direction and are provided in the area between the fastening tapes such that one of the extensible side parts is in a first side flap in the longitudinal end section having the fastening tapes, and the other extensible side part is in a second side flap in the longitudinal end section having the fastening tapes.

3. The disposable diaper according to claim 1, wherein a ratio of a distance W3 from a fixed end of one of the standing gathers to the nearest arched side edge of the crotch section thereto, in the minimum width W1 of the crotch section, to the whole width W2 of the diaper, W3/W2, is from 0.1 to 0.2.

4. The disposable diaper according to claim 1, wherein the minimum width W1 of the crotch section of the diaper is from 100 to 240 mm.

5. The disposable diaper according to claim 1, wherein means for tearing the diaper is provided in both side parts of the diaper that are between the fastening tapes and which are configured to be brought into contact with a side of the wearer.

6. The disposable diaper according to claim 1, wherein the fastening tape has a turn-up tab at a free end thereof.

* * * * *